(12) United States Patent
Penland

(10) Patent No.: US 10,569,069 B2
(45) Date of Patent: Feb. 25, 2020

(54) APPLICATOR FOR TREATMENTS APPLIED TO ANIMAL SKIN

(71) Applicant: Combat Comb, LLC, Cherry Hill, NJ (US)

(72) Inventor: Brandon Penland, Linwood, NJ (US)

(73) Assignee: COMBAT COMB, LLC, Cherry Hill, NJ (US)

( * ) Notice: Subject to any disclaimer, the term of this patent is extended or adjusted under 35 U.S.C. 154(b) by 626 days.

(21) Appl. No.: 15/378,220

(22) Filed: Dec. 14, 2016

(65) Prior Publication Data

US 2018/0161558 A1 Jun. 14, 2018

(51) Int. Cl.
| | | |
|---|---|---|
| *A61M 35/00* | (2006.01) | |
| *A01K 13/00* | (2006.01) | |
| *A61D 7/00* | (2006.01) | |

(52) U.S. Cl.
CPC ......... *A61M 35/003* (2013.01); *A01K 13/003* (2013.01); *A61D 7/00* (2013.01); *A61M 2250/00* (2013.01)

(58) Field of Classification Search
CPC ... A61M 35/003; A61M 2250/00; A61D 7/00; A91K 13/003; A01K 13/003
See application file for complete search history.

(56) References Cited

U.S. PATENT DOCUMENTS

| | | |
|---|---|---|
| D34,664 S | 6/1901 | Poe |
| 713,530 A | 11/1902 | Herfert |
| D47,182 S | 4/1915 | Danziger |
| 1,545,476 A | 7/1925 | Austerman |
| 1,568,319 A | 1/1926 | Cogswell |
| D85,955 S | 1/1932 | Payne |
| 1,851,859 A | 3/1932 | Marshall |
| 1,868,429 A | 7/1932 | Pasley |
| 1,974,656 A | 9/1934 | Nelson |
| 1,989,847 A | 2/1935 | Cowdery |
| D119,332 S | 3/1940 | Forrest et al. |
| D119,333 S | 3/1940 | Forrest et al. |
| D132,131 S | 4/1942 | Mull |
| 2,409,432 A | 10/1946 | Hubbard |
| 2,702,020 A | 2/1955 | Worden |
| 2,725,058 A | 11/1955 | Rathkey |
| 3,063,191 A | 11/1962 | Main |
| D202,754 S | 11/1965 | Naftolin et al. |
| 3,246,425 A | 4/1966 | Miller |
| D208,611 S | 9/1967 | Smith, Jr. |
| 3,425,695 A | 2/1969 | Kestenbaum |
| 3,454,006 A | 7/1969 | Langdon |
| 3,454,278 A | 7/1969 | Cooper et al. |
| D217,702 S | 5/1970 | Volk et al. |
| 3,512,524 A | 5/1970 | Drewe |

(Continued)

FOREIGN PATENT DOCUMENTS

EP 1002477 A1 5/2000

*Primary Examiner* — Tatyana Zalukaeva
*Assistant Examiner* — Gabriella E Burnette
(74) *Attorney, Agent, or Firm* — Eckert Seamans Cherin & Mellott, LLC

(57) ABSTRACT

An applicator including a body with a hair separator and an application aperture. The hair separator and the application aperture are structured to expose a portion of the animal's skin so that the user can see how much of a treatment is being applied and ensure the treatment is applied substantially to the animal's skin.

5 Claims, 5 Drawing Sheets

(56) References Cited

U.S. PATENT DOCUMENTS

| | | |
|---|---|---|
| 3,537,451 A | 11/1970 | Beck et al. |
| D220,555 S | 4/1971 | Reiterman et al. |
| 3,589,361 A | 6/1971 | Loper et al. |
| 3,596,910 A | 8/1971 | Rizzo |
| D223,043 S | 2/1972 | Raines |
| 3,640,275 A | 2/1972 | Burke et al. |
| 3,651,807 A | 3/1972 | Huggins |
| D224,727 S | 9/1972 | Rychlik |
| D228,691 S | 10/1973 | Stocton |
| 3,782,383 A | 1/1974 | Thompson et al. |
| 3,809,081 A | 5/1974 | Loveless |
| 3,812,612 A | 5/1974 | Petrusek |
| 3,839,818 A | 10/1974 | Heggedal |
| 3,949,751 A | 4/1976 | Birch et al. |
| 3,995,597 A | 12/1976 | Warwick |
| 4,129,128 A | 12/1978 | McFarlane |
| 4,170,993 A | 10/1979 | Alvarez |
| D254,559 S | 3/1980 | Chmela |
| 4,192,304 A | 3/1980 | Millet |
| 4,194,504 A | 3/1980 | Harms et al. |
| 4,200,096 A | 4/1980 | Charvin |
| D257,885 S | 1/1981 | Kulle |
| D258,387 S | 2/1981 | De Frank |
| 4,292,757 A | 10/1981 | Cahen, Jr. |
| 4,311,137 A | 1/1982 | Gerard |
| 4,324,236 A | 4/1982 | Gordon et al. |
| 4,326,519 A | 4/1982 | D'Alo et al. |
| 4,352,354 A | 10/1982 | Ujihara |
| 4,353,369 A | 10/1982 | Muetterties et al. |
| 4,362,156 A | 12/1982 | Feller, Jr. et al. |
| 4,377,052 A | 3/1983 | BonDurant |
| 4,388,074 A | 6/1983 | Seberg et al. |
| 4,389,210 A | 6/1983 | Genese |
| 4,445,893 A | 5/1984 | Bodicky |
| 4,496,348 A | 1/1985 | Genese et al. |
| 4,512,690 A | 4/1985 | Johnson |
| D283,921 S | 5/1986 | Dyak |
| D284,030 S | 5/1986 | McFarlane |
| 4,608,045 A | 8/1986 | Fretwell |
| 4,617,875 A | 10/1986 | Holland |
| D287,882 S | 1/1987 | Glash et al. |
| D288,005 S | 1/1987 | Glash et al. |
| 4,655,720 A | 4/1987 | Renger et al. |
| 4,698,057 A | 10/1987 | Joishy |
| 4,708,716 A | 11/1987 | Sibalis |
| 4,710,175 A | 12/1987 | Cartmell et al. |
| 4,743,265 A | 5/1988 | Whitehouse et al. |
| 4,758,225 A | 7/1988 | Cox et al. |
| 4,775,367 A | 10/1988 | Schmidt |
| 4,799,456 A | 1/1989 | Young |
| 4,813,939 A | 3/1989 | Marcus |
| 4,840,613 A | 6/1989 | Balbierz |
| 4,842,591 A | 6/1989 | Luther |
| 4,863,432 A | 9/1989 | Kvalo |
| 4,917,668 A | 4/1990 | Haindl |
| 4,958,596 A | 9/1990 | Belan |
| 4,969,876 A | 11/1990 | Patterson |
| D315,407 S | 3/1991 | Bradrick et al. |
| D315,822 S | 3/1991 | Ryan |
| 5,027,747 A | 7/1991 | Talley |
| 5,030,212 A | 7/1991 | Rose |
| 5,067,946 A | 11/1991 | Zhadanov |
| 5,078,639 A | 1/1992 | Kippen |
| 5,088,982 A | 2/1992 | Ryan |
| 5,100,357 A | 3/1992 | MacCready et al. |
| D326,154 S | 5/1992 | Deguchi et al. |
| 5,112,312 A | 5/1992 | Luther |
| D327,321 S | 6/1992 | Russell et al. |
| 5,120,320 A | 6/1992 | Fayngold |
| 5,147,319 A | 9/1992 | Ishikawa et al. |
| 5,147,327 A | 9/1992 | Johnson |
| 5,149,328 A | 9/1992 | Zaha |
| 5,154,432 A | 10/1992 | Saunders |
| 5,163,913 A | 11/1992 | Rantanen-Lee et al. |
| 5,167,635 A | 12/1992 | Haber et al. |
| 5,167,647 A | 12/1992 | Wijkamp et al. |
| 5,176,655 A | 1/1993 | McCormick et al. |
| 5,192,275 A | 3/1993 | Burns |
| 5,215,532 A | 6/1993 | Atkinson |
| D338,728 S | 8/1993 | Russell |
| D340,111 S | 10/1993 | Yoshikawa |
| 5,267,971 A | 12/1993 | Brimhall |
| 5,304,144 A | 4/1994 | Brimhall |
| 5,306,253 A | 4/1994 | Brimhall |
| 5,306,258 A | 4/1994 | de la Fuente |
| 5,307,953 A | 5/1994 | Regan |
| 5,330,449 A | 7/1994 | Prichard et al. |
| 5,361,947 A * | 11/1994 | Lifshey ............... B65D 47/10 206/532 |
| D355,031 S | 1/1995 | Yoshikawa |
| 5,380,293 A | 1/1995 | Grant |
| 5,380,301 A | 1/1995 | Prichard et al. |
| 5,382,240 A | 1/1995 | Lam |
| D358,465 S | 5/1995 | Klein et al. |
| D361,797 S | 8/1995 | Kulik |
| 5,484,420 A | 1/1996 | Russo |
| 5,489,273 A | 2/1996 | Whitney et al. |
| 5,498,247 A | 3/1996 | Brimhall |
| 5,501,672 A | 3/1996 | Firth et al. |
| 5,536,255 A | 7/1996 | Moss |
| D381,419 S | 7/1997 | Musgrave et al. |
| 5,651,776 A | 7/1997 | Appling et al. |
| 5,669,803 A | 9/1997 | Sweed |
| 5,674,201 A | 10/1997 | Steinman |
| 5,676,656 A | 10/1997 | Brimhall |
| 5,697,914 A | 12/1997 | Brimhall |
| 5,702,362 A | 12/1997 | Herold et al. |
| D390,107 S | 2/1998 | Hundertmark et al. |
| 5,725,410 A | 3/1998 | Robinson et al. |
| D393,419 S | 4/1998 | Hundertmark et al. |
| 5,743,891 A | 4/1998 | Tolkoff et al. |
| D394,085 S | 5/1998 | Leedy |
| 5,746,215 A | 5/1998 | Manjarrez |
| D395,501 S | 6/1998 | Erskine et al. |
| 5,800,410 A | 9/1998 | Gawreluk |
| 5,807,342 A | 9/1998 | Musgrave et al. |
| 5,814,021 A | 9/1998 | Balbierz |
| D399,539 S | 10/1998 | Smith et al. |
| D403,370 S | 12/1998 | Bottelsen |
| D403,405 S | 12/1998 | Terwilliger |
| D408,530 S | 4/1999 | Eliasen et al. |
| 5,893,484 A | 4/1999 | Fuch et al. |
| 5,908,341 A | 6/1999 | dasa |
| D417,471 S | 12/1999 | Stark |
| 6,048,246 A | 4/2000 | Forti et al. |
| D425,943 S | 5/2000 | Kurtz |
| 6,065,472 A | 5/2000 | Anderson et al. |
| 6,074,265 A | 6/2000 | Barthold |
| 6,102,765 A | 8/2000 | Forti et al. |
| 6,139,392 A | 10/2000 | Walker et al. |
| 6,139,532 A | 10/2000 | Howell et al. |
| D433,503 S | 11/2000 | Powers et al. |
| 6,145,703 A | 11/2000 | Opperman |
| 6,203,456 B1 | 3/2001 | Ossege |
| 6,210,371 B1 | 4/2001 | Shaw |
| 6,228,060 B1 | 5/2001 | Howell |
| D446,720 S | 8/2001 | Qvortrup |
| 6,283,950 B1 | 9/2001 | Appling |
| D448,842 S | 10/2001 | Madsen et al. |
| D450,118 S | 11/2001 | Hyde |
| D450,119 S | 11/2001 | Rose et al. |
| D450,382 S | 11/2001 | Nestenborg |
| D451,599 S | 12/2001 | Crawford et al. |
| D451,600 S | 12/2001 | Crawford et al. |
| D451,601 S | 12/2001 | Crawford et al. |
| D451,999 S | 12/2001 | Crawford et al. |
| D452,000 S | 12/2001 | Crawford et al. |
| D452,312 S | 12/2001 | Crawford et al. |
| D452,413 S | 12/2001 | Rae |
| D454,637 S | 3/2002 | Nestenborg |
| 6,367,421 B1 | 4/2002 | Deacon |
| D458,994 S | 6/2002 | Cindrich |
| D459,802 S | 7/2002 | Cindrich |
| D462,765 S | 9/2002 | Niermann et al. |

(56) References Cited

U.S. PATENT DOCUMENTS

| | | |
|---|---|---|
| 6,443,152 B1 | 9/2002 | Lockhart et al. |
| D465,571 S | 11/2002 | Niermann et al. |
| D469,528 S | 1/2003 | Niermann et al. |
| D469,529 S | 1/2003 | Niermann et al. |
| D471,979 S | 3/2003 | Wilkinson et al. |
| 6,527,747 B2 | 3/2003 | Adams et al. |
| D480,140 S | 9/2003 | Harding et al. |
| 6,626,379 B1 | 9/2003 | Ritsche et al. |
| 6,629,956 B1 | 10/2003 | Polidoro et al. |
| 6,644,309 B2 | 11/2003 | Casper et al. |
| 6,719,727 B2 | 4/2004 | Brimhall et al. |
| D491,266 S | 6/2004 | Cindrich et al. |
| D492,031 S | 6/2004 | Cindrich et al. |
| D498,844 S | 11/2004 | Diamond et al. |
| 6,840,920 B2 | 1/2005 | Millerd |
| D505,202 S | 5/2005 | Chesnin |
| D506,548 S | 6/2005 | Andrews et al. |
| D515,211 S | 2/2006 | Chesnin |
| D539,903 S | 4/2007 | Strong |
| D540,468 S | 4/2007 | Mori |
| D546,446 S | 7/2007 | Chesnin |
| 7,258,685 B2 | 8/2007 | Kerr |
| D553,737 S | 10/2007 | Rolfe |
| D561,896 S | 2/2008 | Jones |
| D572,820 S | 7/2008 | Gallogly et al. |
| 7,422,573 B2 | 9/2008 | Wilkinson et al. |
| D579,561 S | 10/2008 | Call et al. |
| D590,057 S | 4/2009 | Lulla et al. |
| D590,499 S | 4/2009 | Chesnin |
| D592,302 S | 5/2009 | Stokes et al. |
| 7,578,805 B2 | 8/2009 | Hwang |
| 7,606,609 B2 | 10/2009 | Muranushi et al. |
| D604,411 S | 11/2009 | Gomez |
| 7,611,486 B2 | 11/2009 | Jones et al. |
| D607,100 S | 12/2009 | Uchida et al. |
| 7,625,357 B2 | 12/2009 | Yang |
| D608,886 S | 1/2010 | Rueckert et al. |
| D612,938 S | 3/2010 | Grogan |
| 7,670,317 B2 | 3/2010 | Cindrich et al. |
| 7,678,076 B2 | 3/2010 | Crawford |
| 7,691,088 B2 | 4/2010 | Howell |
| D615,649 S | 5/2010 | Zinn et al. |
| D617,447 S | 6/2010 | Hajarian et al. |
| 7,753,878 B2 | 7/2010 | Jones et al. |
| D625,004 S | 10/2010 | McGrady et al. |
| D625,409 S | 10/2010 | Chesnin et al. |
| D625,410 S | 10/2010 | Chesnin et al. |
| 7,806,869 B2 | 10/2010 | Nilsson et al. |
| 7,806,878 B2 | 10/2010 | Cascio |
| 7,824,378 B2 | 11/2010 | Jones et al. |
| 8,007,337 B1 | 8/2011 | DeMasi, Sr. |
| 8,052,649 B2 | 11/2011 | Wright |
| 8,066,670 B2 | 11/2011 | Cluff et al. |
| D654,586 S | 2/2012 | Hogerwerf et al. |
| 8,113,731 B2 | 2/2012 | Cable, Jr. et al. |
| D673,227 S | 12/2012 | Robins et al. |
| 8,337,461 B2 | 12/2012 | Burkholz |
| 8,348,789 B1 | 1/2013 | Walterscheid |
| 8,357,121 B2 | 1/2013 | Burkholz |
| D682,422 S | 5/2013 | Anderson et al. |
| D684,258 S | 6/2013 | Luethy et al. |
| 8,500,690 B2 | 8/2013 | Crawford |
| 8,585,655 B2 | 11/2013 | Bierman |
| 8,591,473 B2 | 11/2013 | Jones et al. |
| D701,956 S | 4/2014 | Bengochea et al. |
| D711,749 S | 8/2014 | Kim et al. |
| D715,423 S | 10/2014 | Rogers |
| D715,931 S | 10/2014 | Watanabe et al. |
| 8,974,407 B2 | 3/2015 | Finke |
| D726,906 S | 4/2015 | Reed |
| D729,065 S | 5/2015 | Muhl et al. |
| D731,641 S | 6/2015 | Du |
| D732,160 S | 6/2015 | Du |
| D732,658 S | 6/2015 | Bengochea et al. |
| D749,214 S | 2/2016 | Uenishi et al. |
| 9,248,234 B2 | 2/2016 | Barron |
| 9,259,533 B2 | 2/2016 | Weilbacher et al. |
| D752,215 S | 3/2016 | Blennow et al. |
| 9,278,180 B2 | 3/2016 | Wong |
| D769,444 S | 10/2016 | Mosler et al. |
| 9,468,740 B2 | 10/2016 | Bierman et al. |
| 9,480,821 B2 | 11/2016 | Ciccone et al. |
| D775,330 S | 12/2016 | Blennow et al. |
| 9,522,254 B2 | 12/2016 | Belson |
| D777,325 S | 1/2017 | Aneas |
| D780,914 S | 3/2017 | Kyvik et al. |
| D782,658 S | 3/2017 | Young |
| 9,623,192 B2 | 4/2017 | Chin et al. |
| 9,662,441 B2 | 5/2017 | Vaillancourt et al. |
| 9,682,329 B1 | 6/2017 | Goitein |
| 9,700,701 B2 | 7/2017 | Benjamin et al. |
| D793,552 S | 8/2017 | Schiller et al. |
| 9,730,729 B2 | 8/2017 | Kilcoin et al. |
| 9,731,097 B2 | 8/2017 | Andino et al. |
| D804,663 S | 12/2017 | Jenkins |
| D808,013 S | 1/2018 | Chheda et al. |
| 9,861,784 B2 | 1/2018 | Wilkinson |
| 9,878,130 B2 | 1/2018 | Crawford |
| 9,924,898 B2 | 3/2018 | Hwang et al. |
| D817,482 S | 5/2018 | Howell et al. |
| 9,962,526 B2 | 5/2018 | White et al. |
| D819,802 S | 6/2018 | Burkholz et al. |
| 2002/0068921 A1 | 6/2002 | McWethy et al. |
| 2003/0083620 A1 | 5/2003 | Luther et al. |
| 2003/0131864 A1* | 7/2003 | Lu .................. A45D 19/02 132/108 |
| 2003/0171721 A1 | 9/2003 | Enomoto et al. |
| 2004/0097890 A1 | 5/2004 | Wilkinson |
| 2004/0102735 A1 | 5/2004 | Moulton et al. |
| 2004/0192157 A1 | 9/2004 | Zwiegers |
| 2004/0199124 A1 | 10/2004 | Conte |
| 2004/0222316 A1 | 11/2004 | Scholz |
| 2005/0209583 A1 | 9/2005 | Powers et al. |
| 2006/0116645 A1 | 6/2006 | Whitfield et al. |
| 2006/0184129 A1 | 8/2006 | Bierman |
| 2007/0052926 A1 | 3/2007 | Li |
| 2007/0060897 A1 | 3/2007 | Wang |
| 2007/0060905 A1 | 3/2007 | Howell |
| 2007/0173359 A1 | 7/2007 | Mowery et al. |
| 2007/0191758 A1 | 8/2007 | Hunter et al. |
| 2007/0208310 A1 | 9/2007 | Stadick |
| 2007/0250037 A1 | 10/2007 | Brimhall et al. |
| 2007/0260221 A1 | 11/2007 | Chesnin |
| 2008/0021422 A1 | 1/2008 | Couasnon et al. |
| 2008/0038298 A1 | 2/2008 | Barnikol-Keuten et al. |
| 2008/0045894 A1 | 2/2008 | Perchik et al. |
| 2008/0046004 A1 | 2/2008 | Stenton |
| 2008/0051729 A1 | 2/2008 | Cheng |
| 2008/0132141 A1 | 6/2008 | Dorius |
| 2008/0272209 A1 | 11/2008 | Yokoyama et al. |
| 2008/0319387 A1 | 12/2008 | Amisar et al. |
| 2009/0105673 A1* | 4/2009 | Cascio .................. A45D 34/00 604/310 |
| 2009/0287189 A1 | 11/2009 | Suwito |
| 2010/0087790 A1* | 4/2010 | Hurwitz .............. A01K 13/003 604/310 |
| 2010/0136873 A1 | 6/2010 | Hollis |
| 2010/0266981 A1 | 10/2010 | Levine |
| 2011/0054403 A1 | 3/2011 | Tanabe et al. |
| 2011/0092922 A1 | 4/2011 | Trompen et al. |
| 2011/0160671 A1 | 6/2011 | Tanabe et al. |
| 2012/0016265 A1 | 1/2012 | Peterson et al. |
| 2012/0061286 A1 | 3/2012 | De Menezes et al. |
| 2012/0265159 A1 | 10/2012 | Kaufman |
| 2013/0004229 A1 | 1/2013 | Kirk, III et al. |
| 2013/0079735 A1* | 3/2013 | Hartman .............. A01K 13/003 604/310 |
| 2013/0218082 A1 | 8/2013 | Hyer et al. |
| 2014/0031768 A1 | 1/2014 | Takaki |
| 2014/0330234 A1* | 11/2014 | Schonbeck ....... A61F 13/15699 604/365 |
| 2015/0151209 A1 | 6/2015 | Mullaney et al. |
| 2015/0306349 A1 | 10/2015 | Bonnal |
| 2015/0327653 A1 | 11/2015 | Decaux et al. |

(56) References Cited

U.S. PATENT DOCUMENTS

| | | |
|---|---|---|
| 2015/0360014 A1 | 12/2015 | Decaux et al. |
| 2016/0339221 A1* | 11/2016 | Patterson ............ A61M 35/003 |
| 2017/0120008 A1 | 5/2017 | Burkholz et al. |
| 2017/0120014 A1 | 5/2017 | Harding et al. |
| 2017/0266383 A1 | 9/2017 | Youssefirad |
| 2017/0281870 A1 | 10/2017 | Kai et al. |
| 2018/0001036 A1 | 1/2018 | Shah |

* cited by examiner

APPLICATOR FOR TREATMENTS APPLIED TO ANIMAL SKIN

BACKGROUND OF THE INVENTION

Field of the Invention

The disclosed and claimed concept relates to an applicator for treatments applied to an animal's skin and, more particularly, to an applicator structured to separate an animal's hair thereby substantially exposing the skin.

Background Information

Many treatments, such as, but not limited to, medicines, pest repellants, balms, salves, ointments, gels, and oils, are intended to be applied to an animal's skin (collectively hereinafter a "treatment"). The skin on many animals, however, is covered with a coat such as, but not limited to, hair, fur, or feathers (collectively, and as used herein, "hair"). The hair substantially overlays the animals skin and prevents the direct application of the treatment. This is a notable problem in that a dose of some, but not all, treatments are measured by length, e.g., a treatment is to be applied over "one inch" of the animal's skin.

Initially, users would hold the animal while attempting to part the animal's hair by hand. This method is inefficient as many, but not all, pets are anxious when being held firmly and are likely to fidget or otherwise attempt to escape. Thus, the user would need to wrangle the animal for an extended period of time. Further, a human hand is not likely to part some types of animal hair in such a manner as to expose the animal's skin. Thus, the treatment was likely to be applied to the animal's hair as opposed to the animal's skin. Further, or alternatively, a user who was aware of these problems, could try to apply an excessive amount of the treatment in an attempt to ensure enough treatment reached the animal's skin. This wastes the treatment and could lead to an overdose of the treatment. This process also placed the user's hands and the treatment in immediately proximity to each other and, given a fidgeting pet, the user was likely to spread the treatment to their own fingers. This is notable as some treatments should not be applied to a human's skin. Further, the animal was likely to dislike such a lengthy process and would be less likely to willingly submit to the process again. Thus, the treatment was not applied in an effective manner and the animal was made uncomfortable.

Several devices have been used to assist in applying treatments to an animal's skin. One type of device, as shown in U.S. Pat. No. 5,361,947, includes a number of elongated, rigid conduits coupled to a resilient reservoir. The conduits are inserted through the hair with the tips adjacent the animal's skin. The reservoir is then squeezed and the treatment passes through the conduits. The disadvantage to this type of device is that the person applying the treatment does not see the animal's skin and does not know if the treatment is actually being applied to the animal's skin. As a result, much of the treatment may actually be applied to the animal's hair. Such an improper application reduces the efficacy of the treatment. To ensure that the tips of the conduits are adjacent the animal's skin, some user's apply excessive force to the device and may hurt, or frighten, the animal. Further, the tips of the conduits are also obscured by the animal's hair so it is still difficult, or impossible, to see how much of the treatment is being applied or over what length the treatment is being applied. Thus, in some instances, the treatment was applied over too short/small of an area. That is, the treatment was concentrated in too small of an area of the animal's skin. This could lead to irritation or other problems. Further, depending upon the treatment, the treatment in the tubes needed to be flushed out after each application process. Thus, a portion of the treatment was wasted during each application.

Other devices, such as the applicator disclosed in U.S. Patent Publication 2009/0105673, utilize a plier-like mechanical assembly to separate the hair and expose the skin. The disadvantage to such devices is that action of separating the hair may pull the hair and hurt/frighten the animal. Also, when the device is closed, the animal's hair may become trapped in the moving parts of the device. Further, such devices include springs, or other biasing devices, structured to separate two handles. Thus, a user must maintain a constant pressure on the device so as to keep the animals' hair separated while applying the treatment and while controlling the animal. Further, depending upon the nature (density, amount of curl, etc.) of the animal hair, such devices may not be effective in actually parting the animal's hair. Such devices are also complex; including many parts that must be assembled. This makes such devices expensive and prone to wear and tear. Further, such devices may require the user to restrain an animal for more than a brief period of time. Restraining an animal causes the animal stress. Thus, the time required to use such applicators is a problem.

Further, the various problems identified above lead, either individually or collectively, to the problem of the animal receiving inconsistent doses of the treatment. That is, the treatment is often applied to the animal's hair leading to a low dose. The user may compensate by applying extra treatment which leads to a high dose. Applying an inconsistent dose of a treatment can be harmful to the animal.

There is, therefore, a need for an applicator that exposes an animal's skin, does not include moving parts, and is inexpensive.

SUMMARY OF THE INVENTION

These needs, and others, are met by at least one embodiment of the disclosed and claimed concept which provides an applicator comprising a body including a hair separator and an application aperture. The applicator is, substantially, a unitary body which is inexpensive to make and assemble, which cannot trap an animal's hair during use, and which is less subject to wear and tear. Further, the hair separator and the application aperture are structured to expose a portion of the animal's skin so that the user can see how much treatment is being applied and ensure the treatment is applied substantially to the animal's skin. That is, the user can see that the treatment is not being applied substantially to the animal's hair. Further, use of the applicator allows the user to rapidly part the animal's hair so the length of time for which the animal is restrained is reduced. Further, by applying the treatment through an application aperture, the user's hand(s) is spaced from the exposed treatment. Thus, the user is less likely to come into contact with the treatment. Thus, the configuration of the applicator, as discussed below, solves the problems stated above.

BRIEF DESCRIPTION OF THE DRAWINGS

A full understanding of the invention can be gained from the following description of the preferred embodiments when read in conjunction with the accompanying drawings in which.

Figure 1:
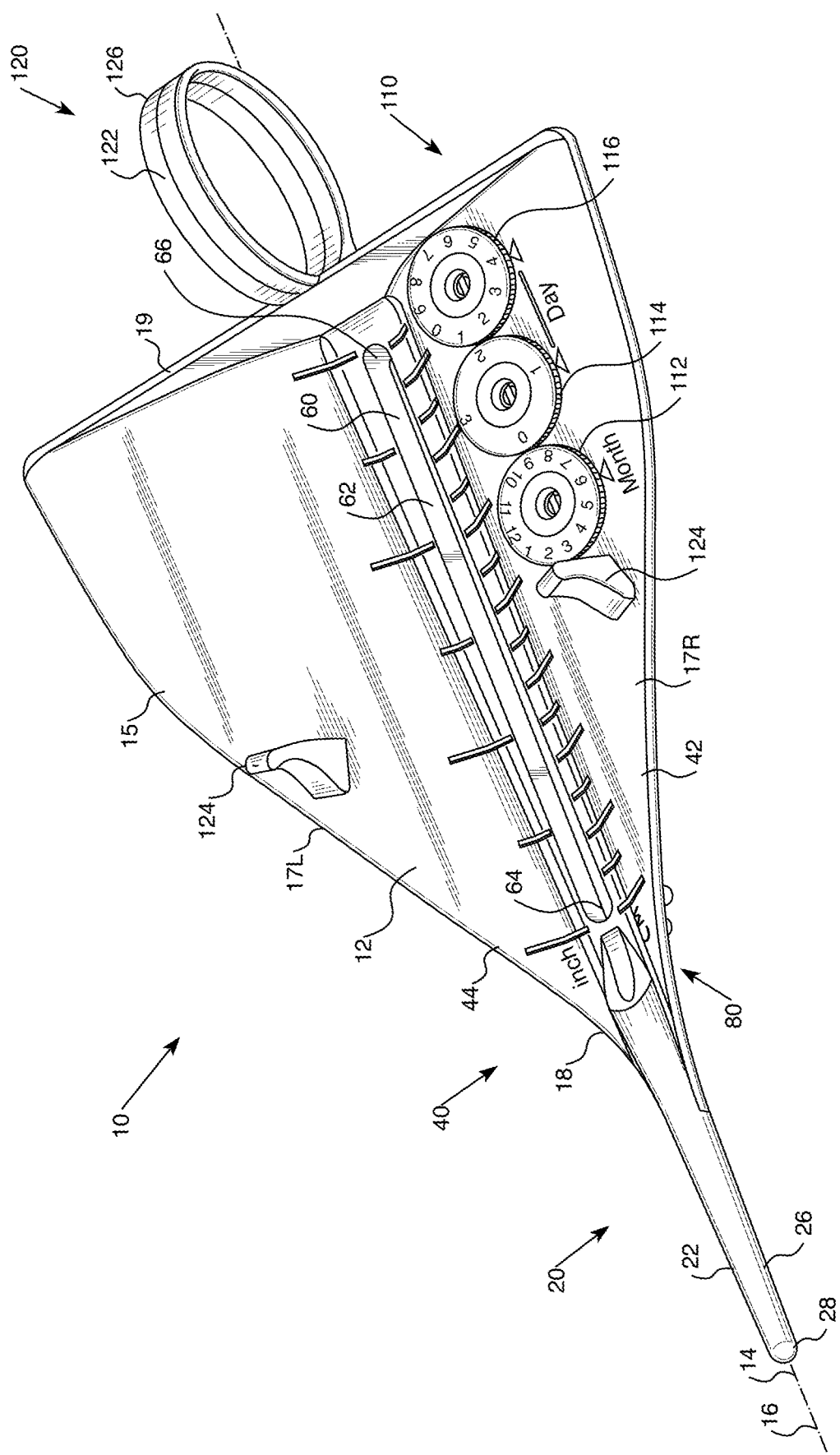
FIG. 1 is an isometric view of an applicator.
Figure 2:
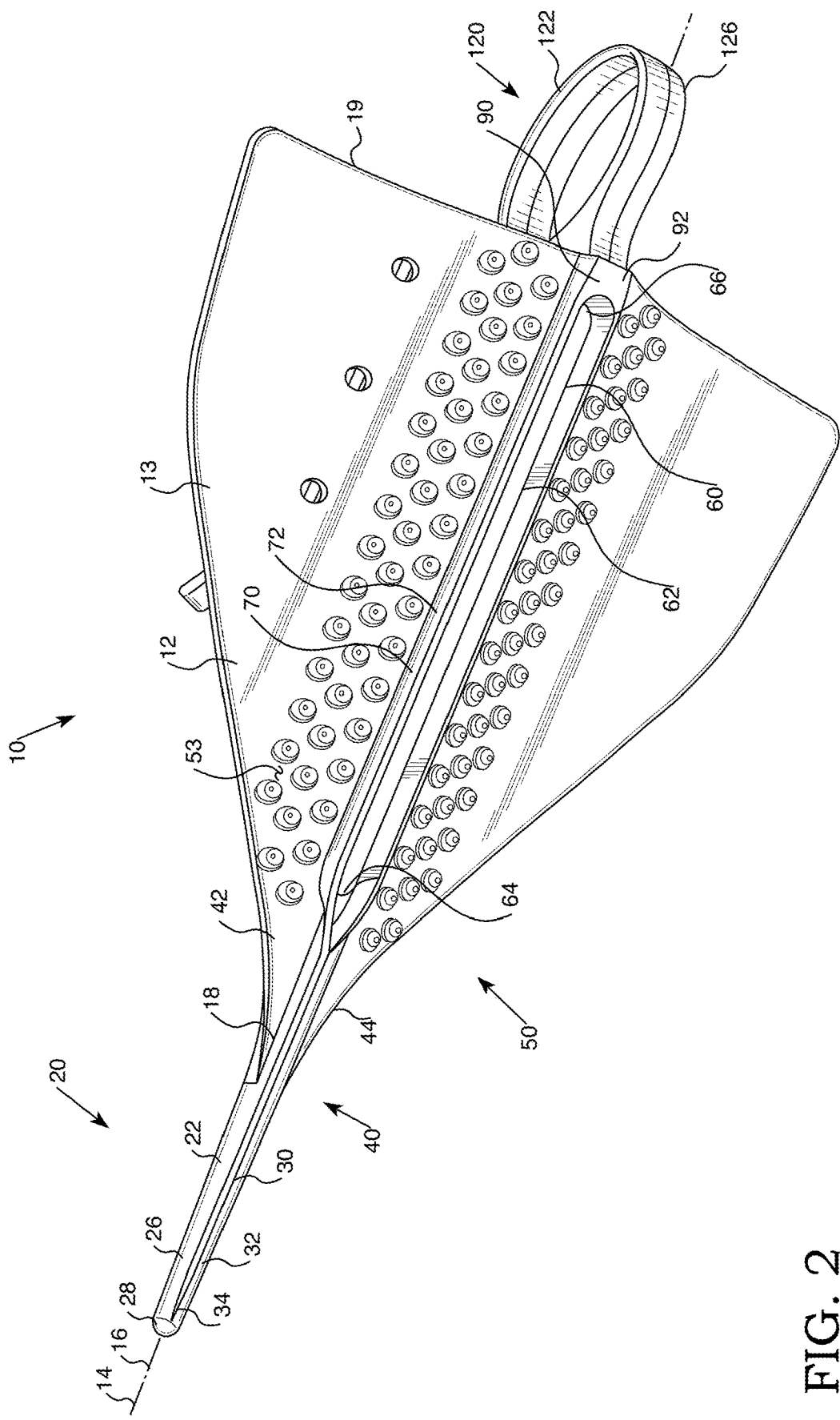
FIG. 2 is another isometric view of an applicator.

DESCRIPTION OF THE PREFERRED
EMBODIMENTS

For purposes of the description hereinafter, directional phrases used herein such as, for example, "clockwise," "counterclockwise," "up," "down," and derivatives thereof shall relate to the disclosed concept, as it is oriented in the drawings. It is to be understood that the specific elements illustrated in the drawings and described in the following specification are simply exemplary embodiments of the disclosed concept. Therefore, specific orientations and other physical characteristics related to the embodiments disclosed herein are not to be considered limiting with respect to the scope of the disclosed concept.

As employed herein, the term "number" shall mean one or an integer greater than one (i.e., a plurality).

As employed herein, the singular form of "a," "an," and "the" include plural references unless the context clearly dictates otherwise.

As employed herein, the statement that two or more parts are "connected" or "coupled" together shall mean that the parts are joined together either directly or joined through one or more intermediate parts. As used herein, "directly coupled" or "directly connected" means that two elements are directly in contact with each other. As used herein, "fixedly coupled" or "fixed" means that two components are coupled so as to move as one while maintaining a constant orientation relative to each other. Accordingly, when two elements are coupled, all portions of those elements are coupled. A description, however, of a specific portion of a first element being coupled to a second element, e.g., an axle first end being coupled to a first wheel, means that the specific portion of the first element is disposed closer to the second element than the other portions thereof. Further, an object resting on another object held in place only by gravity is not "coupled" to the lower object unless the upper object is otherwise maintained substantially in place. That is, for example, a book on a table is not coupled thereto, but a book glued to a table is coupled thereto.

As used herein, the phrase "removably coupled" means that one component is coupled with another component in an essentially temporary manner. That is, the two components are coupled in such a way that the joining or separation of the components is easy and would not damage the components. For example, two components secured to each other with a limited number of readily accessible fasteners, i.e., fasteners that are not difficult to access, are "removably coupled" whereas two components that are welded together or joined by difficult to access fasteners are not "removably coupled." A "difficult to access fastener" is one that requires the removal of one or more other components prior to accessing the fastener wherein the "other component" is not an access device such as, but not limited to, a door.

As employed herein, the statement that two or more parts or components "engage" one another shall mean that the parts touch and/or exert a force against one another either directly or through one or more intermediate parts or components. Further, as used herein with regard to moving parts, a moving part may "engage" another element during the motion from one position to another and/or may "engage" another element once in the described position. Thus, it is understood that the statements, "when element A moves to element A first position, element A engages element B," and "when element A is in element A first position, element A engages element B" are equivalent statements and mean that element A either engages element B while moving to element A first position and/or element A either engages element B while in element A first position.

As used herein, "operatively engage" means "engage and move." That is, "operatively engage" when used in relation to a first component that is structured to move a movable or rotatable second component means that the first component applies a force sufficient to cause the second component to move. For example, a screwdriver may be placed into contact with a screw. When no force is applied to the screwdriver, the screwdriver is merely "coupled" to the screw. If an axial force is applied to the screwdriver, the screwdriver is pressed against the screw and "engages" the screw. However, when a rotational force is applied to the screwdriver, the screwdriver "operatively engages" the screw and causes the screw to rotate. Further, with electronic components, "operatively engage" means that one component controls another component by a control signal or current.

As used herein, "operatively coupled" means that a number of elements or assemblies, each of which is movable between a first position and a second position, or a first configuration and a second configuration, are coupled so that as the first element moves from one position/configuration to the other, the second element moves between positions/configurations as well. It is noted that a first element may be "operatively coupled" to another without the opposite being true.

As used herein, a "coupling assembly" includes two or more couplings or coupling components. The components of a coupling or coupling assembly are generally not part of the same element or other component. As such, the components of a "coupling assembly" may not be described at the same time in the following description.

As used herein, a "coupling" or "coupling component(s)" is one or more component(s) of a coupling assembly. That is, a coupling assembly includes at least two components that are structured to be coupled together. It is understood that the components of a coupling assembly are compatible with each other. For example, in a coupling assembly, if one coupling component is a snap socket, the other coupling component is a snap plug, or, if one coupling component is a bolt, then the other coupling component is a nut.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening. Further, as used herein, "loosely correspond" means that a slot or opening is sized to be larger than an element disposed therein. This means that the increased size of the slot or opening is intentional and is more than a manufacturing tolerance. With regard to surfaces, shapes, and lines, two, or more, "corresponding" surfaces, shapes, or lines have generally the same size, shape, and contours.

As used herein, a "path of travel" or "path," when used in association with an element that moves, includes the space an element moves through when in motion. As such, any element that moves inherently has a "path of travel" or "path." When used in association with an electrical current, a "path" includes the elements through which the current travels.

As used herein, "structured to [verb]" means that the identified element or assembly has a structure that is shaped, sized, disposed, coupled and/or configured to perform the identified verb. For example, a member that is "structured to move" is movably coupled to another element and includes elements that cause the member to move or the member is otherwise configured to move in response to other elements or assemblies. As such, as used herein, "structured to [verb]" recites structure and not function. Further, as used herein, "structured to [verb]" means that the identified element or assembly is intended to, and is designed to, perform the identified verb. Thus, an element that is merely capable of performing the identified verb but which is not intended to, and is not designed to, perform the identified verb is not "structured to [verb]."

As used herein, "associated" means that the elements are part of the same assembly and/or operate together, or, act upon/with each other in some manner. For example, an automobile has four tires and four hub caps. While all the elements are coupled as part of the automobile, it is understood that each hubcap is "associated" with a specific tire.

As used herein, in the phrase "[x] moves between its first position and second position," or, "[y] is structured to move [x] between its first position and second position," "[x]" is the name of an element or assembly. Further, when [x] is an element or assembly that moves between a number of positions, the pronoun "its" means "[x]," i.e., the named element or assembly that precedes the pronoun "its."

As used herein, the word "unitary" means a component that is created as a single piece or unit. That is, a component that includes pieces that are created separately and then coupled together as a unit is not a "unitary" component or body.

As used herein, "about" in a phrase such as "disposed about [an element, point or axis]" or "extend about [an element, point or axis]" or "[X] degrees about an [an element, point or axis]," means encircle, extend around, or measured around. When used in reference to a measurement or in a similar manner, "about" means "approximately," i.e., in an approximate range relevant to the measurement as would be understood by one of ordinary skill in the art.

As used herein, "generally" means "in a general manner" relevant to the term being modified as would be understood by one of ordinary skill in the art.

As used herein, "substantially" means for the most part, by a large amount or degree, as would be understood by one of ordinary skill in the art. Thus, for example, a first element "substantially" disposed in a second element is, for the most part, disposed in the second element.

As shown in FIGS. 1-5, an applicator 10 includes a body 12 having a hair separator 20 and an application aperture 60. Generally, the hair separator 20 is structured to move a first portion of hair on an animal to one side of a part line and a second portion of hair to the other side of the part line. It is understood that some hair may extend from the animal's skin from a location directly on the part line and a portion of these individual hairs is not directed to either side of the line; this amount of hair is, however, minimal and, as used herein, is not a portion of the animal's "hair." Generally, the application aperture 60 is structured to allow the user to insert a treatment, or a container/applicator, through the animal's hair while also making the animal's skin substantially visible or exposed, as defined below.

In an exemplary embodiment, the applicator body 12 is a unitary body or a substantially unitary body. As used herein, a "substantially unitary [applicator] body" means that all the portions of the hair separator 20 and the application aperture 60 are portions of a unitary body. It is understood that other elements, such as, but not limited to, a chronometer assembly 110, discussed below, may not be unitary with a "substantially unitary applicator body" 12. As described below, the applicator body 12 is structured to be drawn through an animal's hair. Thus, the applicator body 12 has an axis of motion 14. In an exemplary embodiment, the applicator body 12 is elongated and the axis of motion 14 generally corresponds to the applicator body longitudinal axis 16. Further, it is understood that a small portion of an animal's body, i.e., the portion of the animal's body under the application aperture 60, is generally planar; a plane parallel to the plane of the animal's skin and extending through the application aperture 60 is, as used herein, the applicator's (or applicator body's 12) "plane of motion." Further, the side of the applicator body 12 that is disposed immediately adjacent the animal is, as used herein, the "applicator body lower side" 13. The side of the applicator body 12 opposite the applicator body lower side 13 is, as used herein, the "applicator body upper side" 15. Further, in the plane of motion and on either side of the applicator body longitudinal axis 16, the applicator body 12 has a right, first lateral side 17R and a left, second lateral side 17L. Further, the applicator body 12 includes a forward side 18 and a trailing side 19. The applicator body forward side 18 is the side towards which the applicator body 12 is pulled during use. The applicator body trailing side 19 is generally opposite the applicator body forward side 18. The axis of motion 14 extends between the applicator body forward side 18 and the applicator body trailing side 19. Further, it is understood that, as the hair separator 20 and the application aperture 60 are part of the applicator body 12, the terms "forward," "trailing," "upper," and "lower" are also, as used herein, applicable to the hair separator 20 and the application aperture 60, and elements thereof. It is common for an animal's hair to have a "lay" or direction. For animals with generally straight hair, the lay is from front to back. Thus, the axis of motion 14, relative to the animal, extends from the back to the front. The elongated applicator 10 describe below, works well with animals have such hair.

For other animals, e.g., animals with curly hair, an elongated applicator 10 with a straight applicator body longitudinal axis 16 may not be the best configuration. Thus, in another embodiment, not shown, the applicator 10 is generally curved or, in an exemplary embodiment, arcuate (e.g., a substantially circular curve). In this embodiment, the applicator (not shown) is rotated through the animal's hair. The elements discussed below, such as but not limited to the hair separator 20, the application aperture 60, are similarly curved.

In an exemplary embodiment, the applicator body upper side 15 includes a measuring indicia 80. As shown, the measuring indicia 80 are marks showing English and Metric length units. Thus, the measuring indicia 80 is disposed adjacent the application aperture 60 and allows a user to see the amount of a treatment applied when measured by length. The measuring indicia 80 is structured to, and does, allow the user to apply a consistent amount of treatment via the application aperture 60. This solves the problems stated above.

The hair separator 20 is structured to move a first portion of hair on an animal to one side of the applicator body longitudinal axis 16 (or axis of motion 14) and a second portion of hair to the other side of the applicator body longitudinal axis 16 (or axis of motion 14). The line between the first and second portions of hair is identified herein as a "part line." As is known, the skin under the hair is substantially exposed at the part line. In an exemplary embodiment, the hair separator 20 includes an initial separator 22 and a parting device 40. The initial separator 22 is structured to move the base of the hair, i.e., the portion of the hair closest to the skin, to one side of the part line. As shown, the initial separator 22 includes an elongated prong 26 extending forwardly, i.e., extending in the forward direction of the axis of motion 14, from the rest of the applicator body 12. Further, the prong 26 includes a rounded, distal end 28. Also, the prong 26 includes a longitudinal ridge 30 on the lower side. The prong longitudinal ridge 30 is, in an exemplary embodiment, disposed along the axis of motion 14. Further, the forward end 32 of the prong longitudinal ridge 30, also identified herein as the leading edge of the prong longitudinal ridge 30, is tapered to a point 34 or a rounded point (not shown).

The hair separator 20 also includes a parting device 40. The parting device is disposed downstream of the initial separator 22. As used herein, "downstream" means that, while in use, an element is contacted later than an "upstream" element. That is, as the applicator body 12 is moved, objects contact the "upstream" elements before the "downstream" elements. Thus, "downstream" elements are disposed closer to the applicator body trailing side 19. The parting device 40 is structured to move and/or maintain a first portion of hair on an animal to one side of the applicator body longitudinal axis 16 (or axis of motion 14) and a second portion of hair to the other side of the applicator body longitudinal axis 16 (or axis of motion 14). In an exemplary embodiment, the parting device 40 includes a first side portion 42 and a second side portion 44. The parting device first side portion 42 is disposed on a first lateral side of the applicator body longitudinal axis 16 (or axis of motion 14). The parting device second side portion 44 is disposed on a second lateral side of the applicator body longitudinal axis 16 (or axis of motion 14). The parting device first side portion 42 and the parting device second side portion 44 are each longitudinally tapered. That is, the parting device first side portion 42 and the parting device second side portion 44 are narrow at the applicator body forward side 18 and wide at the applicator body trailing side 19. Further, in an exemplary embodiment, the parting device first side portion 42 and the parting device second side portion 44 are angled upwardly from the application aperture 60. In this configuration, the parting device 40 parts the animal's hair without hurting the animal and solves the problems stated above.

The parting device 40, i.e., the parting device first side portion 42 and the parting device second side portion 44, also includes a directional construct 50. As used herein, a "directional construct" 50 is a construct structured to move hair to, and/or maintain hair in, a selected location. The directional construct 50, in an exemplary embodiment, is disposed on the lower side of the parting device first side portion 42 and the parting device second side portion 44. For example, the directional construct 50 is selected from the group including, or consisting of, teeth (not shown), bristles (not shown), singular grooves (not shown), and patterned grooves 52. As used herein, "teeth" are constructs such as teeth on a typical comb. The teeth, in one embodiment, are disposed along the forward edge of the parting device first side portion 42 and the parting device second side portion 44. In another embodiment, the teeth are disposed over a substantial portion of the lower side of the parting device first side portion 42 and the parting device second side portion 44. As used herein, "bristles" are constructs such as the bristles on a human hair brush; i.e., stiff filaments extending from the lower side of the parting device first side portion 42 and the parting device second side portion 44. As used herein, "grooves" are channels in the applicator body 12 on the lower side of the parting device first side portion 42 and the parting device second side portion 44. Alternatively, "grooves" are the gaps between adjacent ridges (not shown) on the lower side of the parting device first side portion 42 and the parting device second side portion 44. When the channels are elongated and when the channels do not intersect each other, the channels are "grooves." As used herein, "patterned grooves" 52 are channels 53 that intersect each other. "Patterned grooves" are, in one exemplary embodiment, formed by a plurality of rounded extensions or other protrusions, such as, but not limited to, hemispheres, disposed on the lower side of the parting device first side portion 42 and the parting device second side portion 44.

The application aperture 60 is structured to allow a user to apply a treatment to the animal's skin. That is, the application aperture 60 is an opening through the applicator body 12. In an exemplary embodiment, the application aperture 60 is disposed substantially on the applicator body longitudinal axis 16. Further, the application aperture 60 is elongated and, as such, is selected from the group comprising, or consisting of, a slot (not shown), a finger slot (not shown), a nozzle slot 62, or a tapered slot (not shown). As used herein, a "finger slot" is a slot having a width sized to accommodate a user's finger. That is, the slot is wide enough for a human finger (or thumb) to pass through. A finger slot is useful when applying a treatment that is not harmful for a human to touch and which should be rubbed into the animal's skin. As used herein, a "nozzle slot" 62 is sized to allow a nozzle, e.g., a medicine bottle dropper or similar construct, to pass therethrough. A nozzle slot 62 is useful when applying a treatment that is a non-viscous liquid and which should not be touched by a human. That is, a nozzle slot 62 is too thin to allow a user's finger to pass therethrough so there is a reduced chance that a user's fingers will touch the treatment. As used herein, a "tapered slot" is a slot that is wide at one end and narrow at the other end. Further, in an exemplary embodiment, the application aperture 60 includes a forward edge 64 and a trailing edge 66.

In an exemplary embodiment, the parting device 40 is disposed at the application aperture forward edge 64. As used herein, the "application aperture forward edge" means the forward edge of the construct that defines the application aperture 60. Thus, stated alternately, the application aperture forward edge 64, is also structured to, and does, separate and pin the animal's hair. That is, as used herein, "separate and pin" as used herein means to part the hair in a manner which substantially exposes the animal's skin, and, maintains the animal hair in a parted configuration. As used herein, "substantially exposes the animal's skin" means that the animal hair is parted so that the skin exposed and visible via the application aperture 60. It is understood that some animal hair will originate immediately under the application aperture 60; such hair in the, or visible via the, application aperture 60 does not preclude the skin under the application aperture 60 from being substantially exposed. That is, depending upon the length of the hair, the bulk of each hair will be disposed on either side of the application aperture 60 with just the base visible via the application aperture 60. Thus, while the hair is in the application aperture 60, the animal's skin is still substantially exposed.

In an exemplary embodiment, the application aperture 60 is encircled by a collar 70. That is, a collar 70 is a thicker portion of the applicator body 12 having a vertical sidewall 72 immediately adjacent, and therefore defining, the application aperture 60. As used herein, a "vertical sidewall" means a sidewall that extends generally normal to the skin of the animal when the applicator 10 is in use. This solves the problems stated above. The collar 70 is structured to, and does, maintain a volume of the treatment in the space above the application aperture 60. That is, for example, if the applicator body 12 were generally planar with a minimal thickness, the treatment could move sideways over the applicator body 12 rather than move downwardly to the animal's skin. Thus, the collar 70 is further structured to, and does, maintain a space between the treatment and the user's hands. That is, when the treatment is confined within the collar 70, the user is less likely to come into contact with the treatment. Thus, in an exemplary embodiment, the collar 70 is structured to be, and is, a shield between the treatment and the user's skin. As used herein, a "shield" is a barrier on a tool structured to separate a treatment from the user applying the treatment. Thus, the collar 70 solves some of the problems noted above.

In another exemplary embodiment, the lower surface of the collar 70 at the application aperture trailing edge 66 includes a diffuser 90. As used herein, a "diffuser" 90 is a construct structured to apply bias to and/or spread out a treatment. A diffuser 90 includes, but is not limited to, a convex hemisphere (not shown), a wedge (not shown), or a planar portion 92. In operation, after the user applies the treatment, the user continues to pull the applicator 10 along the axis of motion 14; this action moves the diffuser 90 into contact with the treatment and spreads the treatment over a larger area of the animal's skin, and/or, nibs the treatment into the animal's skin. This solves the problems stated above.

In another embodiment, not shown, the diffuser 90 is movably coupled to the collar 70. That is, for example, the collar 70 includes longitudinal grooves (not shown) extending along the application aperture 60. The diffuser 90 is disposed on a slider (not shown). The slider is movably coupled to the collar at the grooves. That is, the slider include tabs that are structured to, and do, extend into the collar grooves. The slider also includes a lug that extends into, and through, the application aperture 60. In use, a treatment is applied through the application aperture 60 and then the user moves the slider from one end of the application aperture 60 to the other. As the slider moves, the lug biases the treatment against and into the animal's skin and spreads the treatment.

Figure 3:
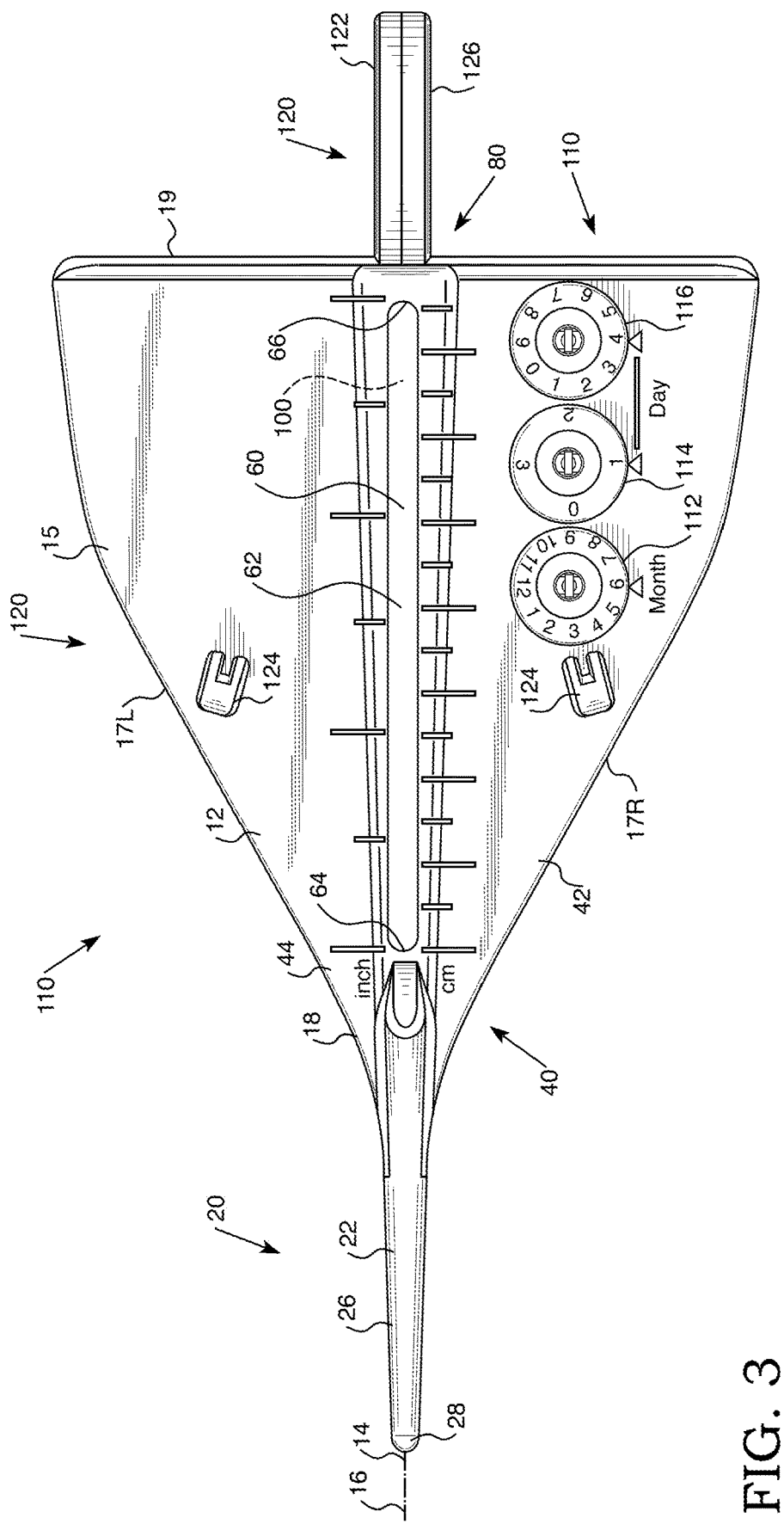
FIG. 3 is a top view of an applicator.
Figure 4:
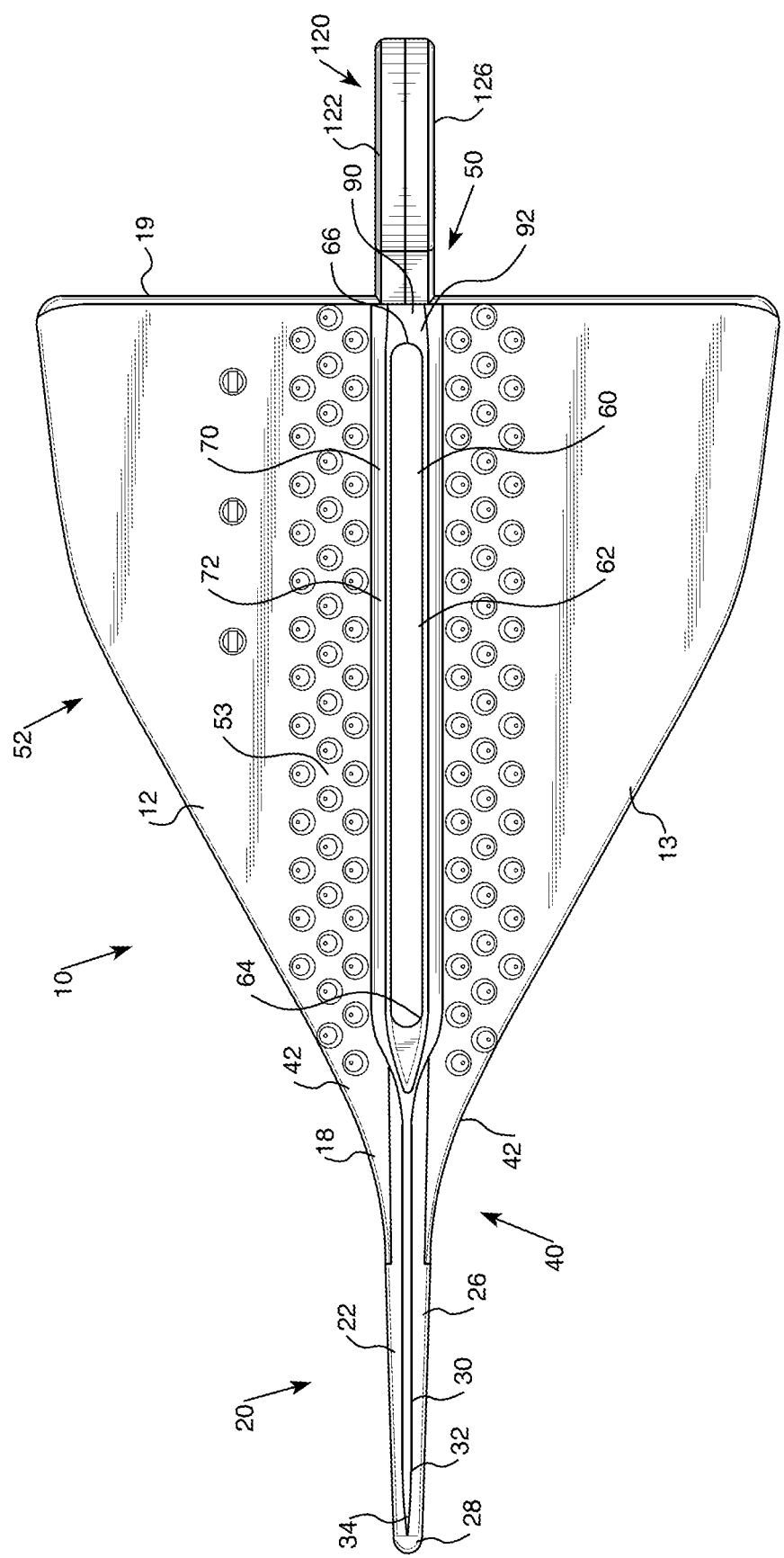
FIG. 4 is a bottom view of an applicator.
Figure 5:
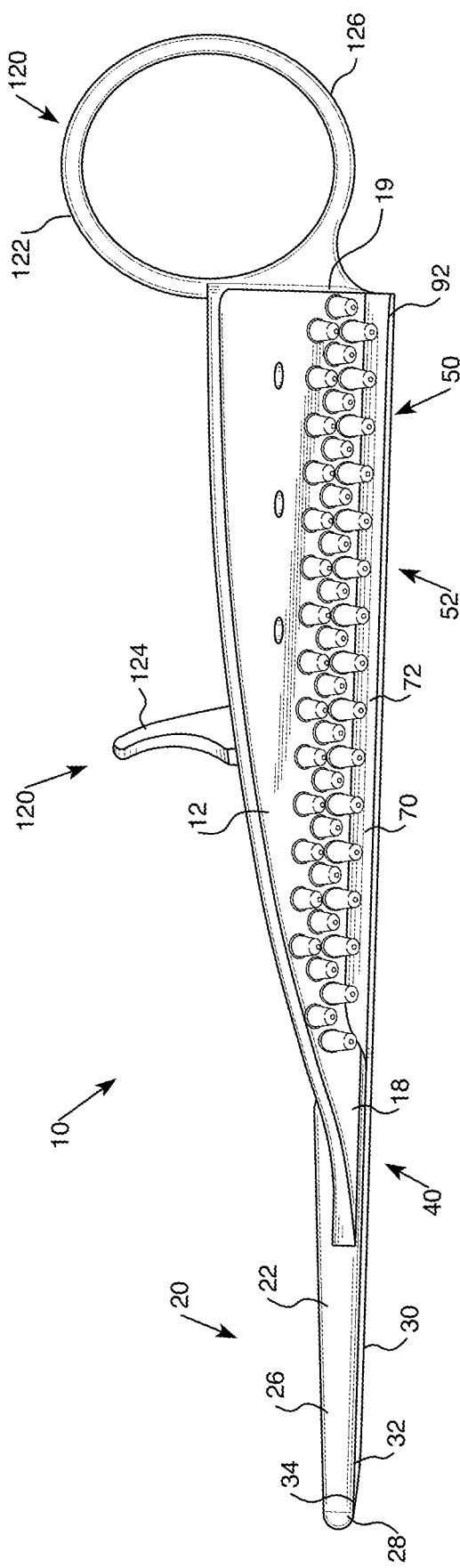
FIG. 5 is a side view of an applicator.

In another embodiment, the application aperture 60 includes a holding construct 100 (FIG. 3, shown in ghost). As used herein, a "holding construct" is an element structured to temporarily hold, contain, and/or support a quantity of the treatment. That is, for example, if the treatment is a medication suspended in a gel, the holding construct 100 is a planar element, or platform, disposed within a finger slot type application aperture 60. In use, the user applies the treatment to the holding construct 100 prior to restraining the animal. Then, after the hair is separated, as described below, the user runs a finger over the holding construct 100 thereby moving the treatment gel off the holding construct 100, through the application aperture 60 and onto the animal's skin. This motion is very quick and, as such, solves the problems stated above. For a liquid treatment, and in one exemplary embodiment, the holding construct is a platform with a concave cavity disposed in the application aperture 60. In an alternative embodiment, the holding construct 100 is a bracket (not shown) structured to hold a container of a liquid treatment. The bracket is positioned to removably couple the container of a liquid treatment to the applicator body 12 with the opening of the container of a liquid treatment disposed in, or near, the application aperture 60. The bracket further includes a pressure surface (not shown). The pressure surface is, in an exemplary embodiment, a surface disposed in a location under the container of a liquid treatment so that a user, during application of the treatment, compresses the container of a liquid treatment against the surface thereby expelling a quantity of the treatment from the container of a liquid treatment.

Alternatively, the applicator 10 includes a guide assembly (not shown) for the treatment. For example, for less viscous or water-like treatments, a funnel is disposed adjacent the application aperture 60. The narrow, exit end of the funnel is disposed within, or immediately adjacent the application aperture 60 while the wide, entry end of the funnel is disposed in an easy to access location above the applicator body upper side 15. Similarly, the guide assembly is, in another embodiment, a watercourse or channel (i.e., a watercourse with upwardly depending sidewalls) extending from a location on the applicator body upper side 15 to a location within the application aperture 60. The watercourse is, in an exemplary embodiment, made from a material that causes water to bead thereon. In this configuration, a water-like liquid applied an upper end of the watercourse or channel will move down the watercourse or channel into the application aperture 60. The upper end of the watercourse or channel is, in an exemplary embodiment, wider than the other portions of the watercourse or channel. Thus, a user does not have to take additional time to insert the treatment applicator into the application aperture 60. This solves some of the problems noted above.

In another embodiment, the applicator 10 includes a chronometer assembly 110. As used herein, a "chronometer assembly" is a construct structured to generally record a date. That is, the "chronometer assembly" does not have to, but may, record a specific date. As shown, the chronometer assembly 110 includes three disks 112, 114, 116 that are rotatably coupled to the applicator body 12. Two of the disks 112, 114 include single digits that, when combined, correspond to a day of the month. That is, a first disk 112 includes the numbers zero (or blank) to three and a second disk 114 includes numbers zero to nine. In this configuration, the first and second disks 112, 114 can be positioned relative to mark(s) on the applicator body 12 to represent days 1-31. The third disk 116 includes numbers one to twelve and represent the months. In another embodiment, the chronometer assembly 110 is a digital chronometer (not shown).

In another embodiment, the applicator 10 includes a grip assembly 120. As used herein, a "grip assembly" is an element that is structured to be grasped by human fingers. Thus, a "grip assembly" is sized, shaped, and positioned, to be grasped by a human hand. An element that is merely capable of being grasped by a human hand but which is not sized, shaped, and positioned, to be grasped by a human hand is not a "grip assembly." In an exemplary embodiment, the grip assembly 120 includes a finger grip 122 and a thumb grip 124. As shown, the finger grip 122 is a ring 126 disposed at the applicator body trailing side 19. In an exemplary embodiment, the ring 126 has s sufficient diameter to accommodate one or two fingers, typically the index and middle fingers, of a human user. That is, the ring 126 has a diameter of between about 1.0 inch to 1.25 inches, or about 1.125 inches. Further, the thumb dip 124 (two shown, one for right handed users and one for left handed users) is an extension extending generally upwardly from the applicator body upper side 15. That is, the thumb grips 124 are, in an exemplary embodiment, disposed generally symmetrically on either side of the applicator body longitudinal axis 16. Further, the forward side of each thumb grip 124 is generally arcuate. In this configuration, the applicator 10 may be used by both left-handed and right-handed users.

In an alternate embodiment, not shown, the grip assembly 120 is structured to allow the user to grip the applicator body trailing side 19 with four fingers. In this embodiment, the grip assembly 120 is structured to generally position the first and second fingers on one lateral side 17L (for right handed users) of the application aperture 60 and to generally position the third and fourth fingers on the other lateral side 17R of the application aperture 60. In another embodiment, not shown, the grip assembly 120 includes a handle or ball grip (neither shown) that extends upwardly from the applicator body upper side 15. The handle is an elongated rod structured to be gripped by a human hand. In an exemplary embodiment, the handle or ball grip is disposed at the application aperture forward edge 64.

In another embodiment, not shown, the grip assembly 120 includes a container mating assembly (not shown). The container mating assembly is structured to, and does, mate with a treatment container. For example, certain treatment containers include a screw on cap that is disposed over a nozzle. For such a treatment container, the mating assembly is a threaded collar disposed at the application aperture forward edge 64. The treatment container is threaded into the threaded collar with the nozzle disposed within, or immediately adjacent, the application aperture 60. Further, in this configuration, the treatment container becomes a grip similar to the handle described above.

In another embodiment, not shown, the applicator 10 includes an illumination assembly, not shown. The illumination assembly is structured to, and does, provide light to the application aperture 60. For example, a light emitting diode (LED) is disposed at the application aperture forward edge 64. A switch (not shown) for the illumination assembly is, in an exemplary embodiment, disposed in the elements of the grip assembly 120.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. An applicator comprising:
    a body including a hair separator and an application aperture;
    wherein said hair separator includes an initial separator and a parting device;
    said body includes a forward side, a trailing side and an axis of motion extending between said forward side and said trailing side;
    said application aperture disposed generally along said body longitudinal axis;
    said parting device includes a first side portion and a second side portion;
    said parting device first side portion disposed on a first lateral side of said body drawing axis;
    said parting device second side portion disposed on a second lateral side of said body drawing axis;
    said parting device is disposed downstream of said initial separator;
    said parting device first side portion and said parting device second side portion each include an upper side and a lower side;
    said parting device first side portion lower side includes a directional construct; and
    said parting device second side portion lower side includes a directional construct.

2. The applicator of claim 1 wherein said parting device first side portion lower side directional construct and said parting device second side portion lower side directional construct is selected from the group including teeth, bristles, singular grooves, and patterned grooves.

3. The applicator of claim 1 wherein said parting device first side portion and said parting device second side portion are each longitudinally tapered.

4. The applicator of claim 1 wherein said parting device first side portion lower side directional construct and said parting device second side portion are each angled upwardly from said application aperture.

5. An applicator comprising:
    a body including a hair separator and an application aperture;
    said body includes a forward side, a trailing side, an upper side, a lower side and a drawing axis extending between said forward side and said trailing side;
    said application aperture includes a forward edge and a trailing edge;
    said body includes a collar extending about said application aperture;
    said collar includes a diffuser; and
    said diffuser disposed at said application aperture trailing edge and on said body lower surface.

* * * * *